(12) United States Patent
Gaston et al.

(10) Patent No.: US 7,432,301 B2
(45) Date of Patent: Oct. 7, 2008

(54) USE OF S-NITROSOTHIOL SIGNALING TO TREAT DISORDERED CONTROL OF BREATHING

(75) Inventors: Benjamin M. Gaston, Charlottesville, VA (US); David Gozal, Louisville, KY (US)

(73) Assignees: University of Virginia Patent Foundation, Charlottesville, VA (US); University of Louisville Research Foundation, Louisville, KY (US)

( * ) Notice: Subject to any disclaimer, the term of this patent is extended or adjusted under 35 U.S.C. 154(b) by 0 days.

(21) Appl. No.: 10/487,060

(22) PCT Filed: Aug. 12, 2002

(86) PCT No.: PCT/US02/25199

§ 371 (c)(1),
(2), (4) Date: Feb. 17, 2004

(87) PCT Pub. No.: WO03/015605

PCT Pub. Date: Feb. 27, 2003

(65) Prior Publication Data

US 2004/0224899 A1    Nov. 11, 2004

Related U.S. Application Data

(60) Provisional application No. 60/313,548, filed on Aug. 20, 2001.

(51) Int. Cl.
*A61K 38/00*   (2006.01)
*A61K 38/05*   (2006.01)
*A61K 38/06*   (2006.01)
*A61K 31/04*   (2006.01)

(52) U.S. Cl. ............................ 514/579; 514/2; 514/18; 514/19; 514/740

(58) Field of Classification Search ............ 128/200.24, 128/200.14, 203.12, 203.15; 514/18, 645
See application file for complete search history.

(56) References Cited

U.S. PATENT DOCUMENTS

| 4,900,719 | A | | 2/1990 | Means et al. |
| 5,380,758 | A | | 1/1995 | Stamler et al. |
| 5,508,045 | A | * | 4/1996 | Harrison et al. ............ 424/608 |
| 5,570,683 | A | | 11/1996 | Zapol et al. |
| 5,574,068 | A | | 11/1996 | Stamler et al. |
| 5,593,876 | A | | 1/1997 | Stamler et al. |
| 5,612,314 | A | | 3/1997 | Stamler et al. |
| 6,314,956 | B1 | | 11/2001 | Stamler et al. |
| 6,331,543 | B1 | | 12/2001 | Garvey et al. |
| 6,352,975 | B1 | * | 3/2002 | Schreiner et al. ............ 514/12 |
| 6,586,478 | B2 | * | 7/2003 | Ackman et al. ............ 514/738 |
| 6,974,814 | B2 | * | 12/2005 | Radulovacki et al. ........ 514/249 |
| 2002/0002136 | A1 | | 1/2002 | Herbert |
| 2002/0106404 | A1 | * | 8/2002 | Lipton ........................ 424/450 |

FOREIGN PATENT DOCUMENTS

WO        WO 92/17455        10/1992

OTHER PUBLICATIONS

Gaston et al., "Stereoselective increase in minute ventilation caused by S-nitroso-L-cysteine administration to the nucleus tractus solitarius of the rat: An hypoxic signalling mechanism?"; Sep. 1999, Acta Physiologica Scandinavica, vol. 167, No. Suppl. 645.*

Weiskopf, R. "Use of Inhaled Nitric Oxide Perioperatively and in Intensive Care Patients", Anesthesiology, 2000, 92(6), pp. 1821-1825.*

Funayama, T., Sekizawa, K., Yamaya, M., Yamauchi, K., Ohno, I., Ohrui, T., Terajima, M., Okinaga, S. and Sasaki, H. (1996). "Role of Leukotriene-degrading Enzymes in Pulmonary Response to Antigen Infusion in Sensitized Guinea Pigs In Vivo." Am. J. Respir. Cell Mol. Biol., vol. 15, pp. 260-267.

Hogg, N., Singh, R. J., Joseph, J. and Kalyanaraman, B. (1997). "S-Nitrosoglutathione as a substrate for gamma-glutamyl transpeptidase." Biochem. J., vol. 323, pp. 477-481.

The Merck Index, 12th edition, items 911 and 917 (1996).

The Merck Index, 11th edition, pp. 14 and 436 (1989).

(Continued)

*Primary Examiner*—Johann Richter
*Assistant Examiner*—James H Alstrum Acevedo
(74) *Attorney, Agent, or Firm*—Rodney L. Sparks

(57) ABSTRACT

The present invention is directed to a method of treating disordered control of breathing including the treatment of apnea and hypoventilation associated with congenital or acquired brain stem abnormalities. Specifically the invention is directed to treating disordered control of breathing by administering an S-nitrosylating agent selected from the group consisting of ethyl nitrite, glutathione, nitric oxide, S-nitrosocysteine, S-nitrosoglutathione, S-nitro-N-acetyl cysteine. As shown in FIG. 1C the ability of endogenous SNO to increase $V_E$ in freely behaving, conscious rates using whole-body plethysmography revealed that CSNO, GSNO and CGSNO (1 nmol each) caused equivalent increases in $V_E$, whereas D-CSNO had no effect (left bar graph is the equivalent increases in $V_E$, whereas D-CSNO had no effect (left bar graph is the control whereas the right bar represents administration of the respective SNO).

5 Claims, 2 Drawing Sheets

OTHER PUBLICATIONS

Gaston, B., Sears, S., Woods, J., Hunt, J., Ponaman, M., McMahon, T. and Stamler, J. S. (1998). "Bronchodilator S-nitrosothiol deficiency in asthmatic respiratory failure." The Lancet. vol. 351, No. 9112, pp. 1317-1319.

Minamiyama, Y., Takemura, S., Koyama, K., Yu, H., Miyamoto, M. and Inoue, M. (1996). "Dynamic aspects of glutathione and nitric oxide metabolism in endotoxemic rats." Am. J. Physiol. vol. 271 (Gastrointest. Liver Physiol. 34): G575-G581.

Aldrich Chemical Company Catalog (1992) p. 15, item 3806-1.

Sigma Catalog (1991) item A7250.

Singh, S. P., Wishnok, J. S., Keshive, M., Deen, W. M. and Tannebaum, S. R. (1996). "The chemistry of the S-nitrosoglutathione/ glutathione system." Pro. Natl. Acad. Sci. USA, vol. 93, pp. 14428-14433.

Singh, R., Hogg, N., Joseph, J. and Kalyanaraman, B. (1996). "Mechanism of Nitric Oxide Release from S-Nitrosothiols." The Journal of Biological Chemistry, vol. 271, No. 31, pp. 18596-18603.

Gaston, B., Reilly, J., Drazen, J. M., Fackler, J., Ramdev, P., Arnelle, D., Mullins, M. E., Sugarbaker, D.J., Chee, C., Singel, D. J., Loscalzo, J. and Stamler, J. S. (1993). "Endogenous nitrogen oxides and bronchodilator S-nitrosothiols in human airways." Proc. Natl. Acad. Sci. USA, vol. 90, pp. 10957-10961.

Stamler, J. S. and Toone, E. J. (2002). "The decomposition of thionitrites." Current Opinion in Chemical Biology, vol. 6, pp. 779-785.

Snyder, D. W., Aharony, D., Dobson, P., Tsai, B. S. and Krell, R. D. (1984). "Pharmacological and Biochemical Evidence for Metabolism Peptide Leukotrienes by Guinea-Pig Airway Smooth Muscle In Vitro." Journal of Pharmacology and Experimental Therapeutics, vol. 231, pp. 224-229.

Nabe, T., Kohno, S., Tanpo, T., Saeki, Y., Yamaura, H., Moriba, M. and Obata, K. (1994). "Inhibitory effect on ONO-1078 on specific binding of peptide leukotrienes to human lung crude membrane." Prostaglandins Leukotrienes & Essential Fatty Acids. vol. 51, No. 3, pp. 163-171.

Gaston, B., Sears, S., Wlton, S., Woods, J., Hunt, J., Arnelle, D. and Stamler, J. S., Mini-Sympsium, p. A945, item D75.

\* cited by examiner

USE OF S-NITROSOTHIOL SIGNALING TO TREAT DISORDERED CONTROL OF BREATHING

RELATED APPLICATION

This application is a national stage filing of International Application No. PCT/US02/25199, filed Aug. 12, 2002, which claims priority under 35 U.S.C. §119(e) to U.S. Provisional Patent Application No. 60/313,548, filed Aug. 20, 2001, the disclosure of which is incorporated herein by reference in its entirety.

US GOVERNMENT RIGHTS

This invention was made with United States Government support under Grant Nos. HL 59337, awarded by the National Institutes of Health. The United States Government has certain rights in the invention.

FIELD OF THE INVENTION

The present invention is directed to compositions and methods for treating disordered control of breathing. More particularly, the present invention is directed to the use of S-nitrosothiols or other S-nitrosylating agents to enhance ventilation in patients suffering from a congenital or acquired brain stem abnormality.

BACKGROUND OF THE INVENTION

The ability to increase minute ventilation ($V_E$=respiratory rate times tidal volume) in response to hypoxia is essential for survival. Failure to breathe more often when oxygen levels are low can contribute to respiratory distress in newborn mammals and to sleep apnea in adults. The mechanisms by which hypoxic stimuli are processed are poorly understood. However, it is known that $V_E$ increases linearly with decreasing oxyhaemoglobin saturation (about 0.6 l/min percent saturation in healthy individuals) and that its regulation involves input to brainstem areas such as the NTS, that are rich in nitric oxide synthase (NOS). This increase in breathing is regulated not only by the mere lack of oxygen, but rather by molecules related to a different gas, nitric oxide (NO), which affect respiratory centers at the base of the brain. These respiratory centers include neurons present in the brain stem as well as those in the carotid body.

Abnormalities of central control of ventilation, particularly in response to hypoxia, can be life-threatening. Central apnea and hypoventilation occur in patients with congenital and acquired brain stem abnormalities, ranging from Arnold Chiari malformation to scar tissue associated with treatment of brainstem tumors. Furthermore, an apneic or hypoventilatory response to hypoxemia can occur in patients with obstructive sleep apnea, and abnormal dependence on hypoxic ventilatory drive can also make oxygen therapy life-threatening in patients with chronic obstructive lung diseases. A newborn infant (particularly the premature and/or anemic infant) can have a paradoxical apneic or hypoventilatory response to hypoxemia that is believed to play a role in the pathogenesis of some cases of Sudden Infant Death Syndrome. Other patients may have profound paradoxical hypoventilation when asleep, as seen in congenital central hypoventilation syndrome.

Current therapeutic options for each of these disorders are limited primarily to techniques involving artificial ventilation. Of note, therapeutic options for respiratory alkalosis associated with acute hyperventilation (whether psychiatric or drug-induced) are similarly limited. The present invention is directed to a novel approach to the treatment of disorders of control of breathing that is based on the use of nitrosylating agents to enhance minute ventilation in such individuals.

SUMMARY OF THE INVENTION

The present invention is directed to a novel approach to treating apnea and hypoventilation associated with congenital or acquired brain stem abnormalities. In particular, applicants have demonstrated that a class of endogenous compounds known as S-nitrosothiols dramatically increases minute ventilation ($V_E$) at the level of the brainstem respiratory control centers in the nucleus tractus solitarius (nTS). In accordance with one embodiment a composition comprising low molecular weight reduced thiols or an S-nitrosylating agent is provided for treating disordered control of breathing.

BRIEF DESCRIPTION OF THE DRAWINGS

FIG. 1A is a graph plotting $V_E$ vs Time and representing the $V_E$ during (shaded) and following a short period of hypoxia. FIG. 1B is a graph plotting $V_E$ vs Time and representing the results obtained after injecting 1 nmol S-Nitrosocysteinyl glycine (CGSNO) into the nucleus tractus solitarius (NTS). A marked increase in $V_E$ (injection indicated by an arrow) was observed with onset and decay characteristics identical to those observed during short exposure of the whole animal to hypoxia and return to normoxia. FIG. 1C is a bar graph representing the data obtained after administering various L-SNO isomers. All L-SNO isomers caused increases in $V_E$ (change from baseline for CGSNO: asterisk, $P<0.001$, $n=10$; S-nitrosoglutathione (GSNO): asterisk, $P<0.0001$, $n=14$; S-nitroso-L-cysteine (L-CSNO): asterisk, $P<0.0001$, $n=20$), whereas S-nitroso-D-cysteine (D-CSNO) was without effect (P=NS; n=20)

FIG. 2A shows that the $V_E$ increases stimulated by microinjection of 10 nmol GSNO were abolished after pre-treatment with the GGT inhibitor acivicin (7.5 nmol; $P<0.0001$; $n=8$). CGSNO (10 nmol) stimulated $V_E$ increases that were not modified by acivicin (P=NS; n=6). FIG. 2B represents the data generated from a hypoxic ventilatory response in GGT-deficient mice (+/+, wild type; +/−, heterozygotes; −/−, GGT-deficient). Lowest $V_E$ during the 30 s after cessation of hypoxia is expressed as percent change from pre-hypoxia baseline ($P<0.0001$; n=8 each group).

DETAILED DESCRIPTION OF THE INVENTION

Definitions

In describing and claiming the invention, the following terminology will be used in accordance with the definitions set forth below.

As used herein, the term "treating" includes alleviating the symptoms associated with a specific disorder or condition and/or preventing or eliminating said symptoms.

As used herein, an "effective amount" means an amount sufficient to produce a selected effect. For example, an effective amount of a S-nitrosylating agent for treating disordered control of breathing is an amount sufficient to alleviating the symptoms associated with disordered control of breathing, including enhancing minute ventilation ($V_E$).

As used herein the term "disordered control of breathing" relates to any disease state or condition that causes a neurological-based loss of the ability to regulate respiration in the afflicted individual. Disorders that relate to the control of breathing include apnea and hypoventilation that is associated with congenital or acquired brain stem abnormalities in addition to neurological abnormalities of nerves innervating respiratory muscles, and nerves signaling from peripheral chemoreceptor. Note that lung disorders can lead to secondary disorders of control of breathing, such as blunted hypoxic ventilatory drive observed in chronic obstructive pulmonary disease.

As used herein the term "nitrosylation" refers to the addition of NO to a thiol group (SH), oxygen, carbon or nitrogen by chemical means. An "S-nitrosylating agent" refers to a compound that can function in vivo to react with protein thiol groups, transferring a NO group to the thiol to form an S-nitrosothiol. Suitable nitrosylating agents are disclosed in Feelisch and Stamler, "Donors of Nitrogen Oxides", Methods in Nitric Oxide Research edited by Feelisch and Stamler, (John Wiley & Sons) (1996), the entire teachings of which are hereby incorporated into this application by reference. S-nitrosylating agents include acidic nitrite, nitrosyl chloride, ethyl nitrite, glutathione, S-nitrosoglutathione, S-nitrosocysteinyl glycine, S-nitrosocysteine, N-acetyl cysteine, S-nitroso-N-acetyl cysteine, nitroglycerine, nitroprusside, nitric oxide, S-nitrosohemoglobin and S-nitrosoalbumin.

As used herein, the term "purified" and like terms relate to the isolation of a molecule or compound in a form that is substantially free (i.e. at least 60% free, preferably 80% free, and most preferably greater than 90% free) from other components with which they are naturally associated.

As used herein, the term "pharmaceutically acceptable carrier" encompasses any of the standard pharmaceutical carriers, such as a phosphate buffered saline solution, water and emulsions such as an oil/water or water/oil emulsion, ethanol and various types of wetting agents.

As used herein, the term "parenteral" includes administration subcutaneously, intravenously or intramuscularly.

The Invention

Figure 1A:
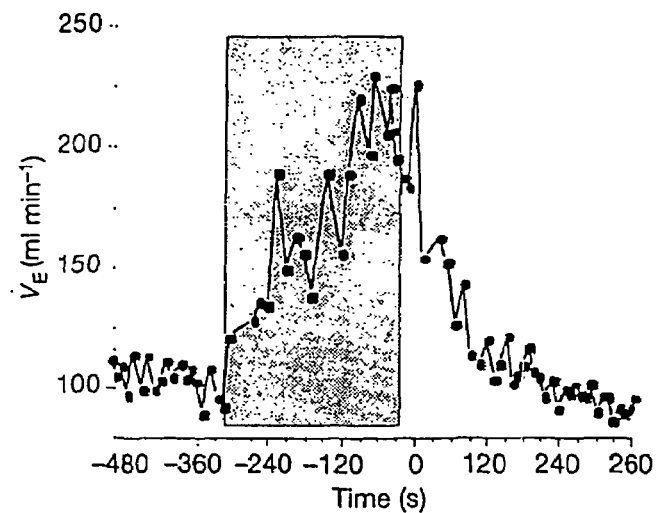
FIGS. 1A-1C Ventilatory effects of SNOs in rats.
Figure 1B:
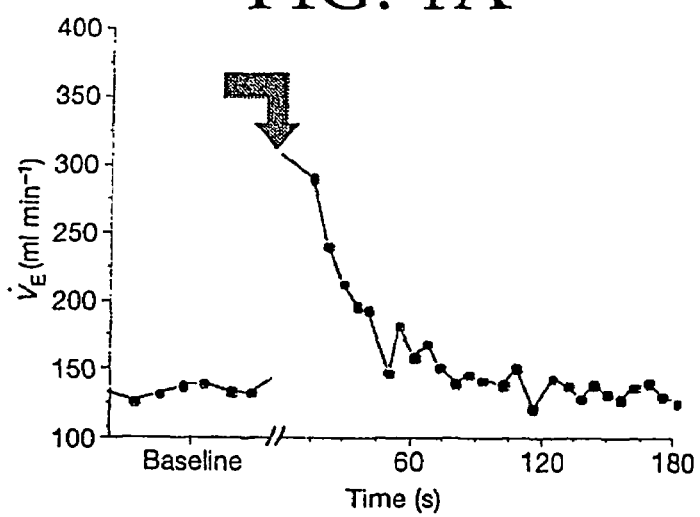
Figure 1C:
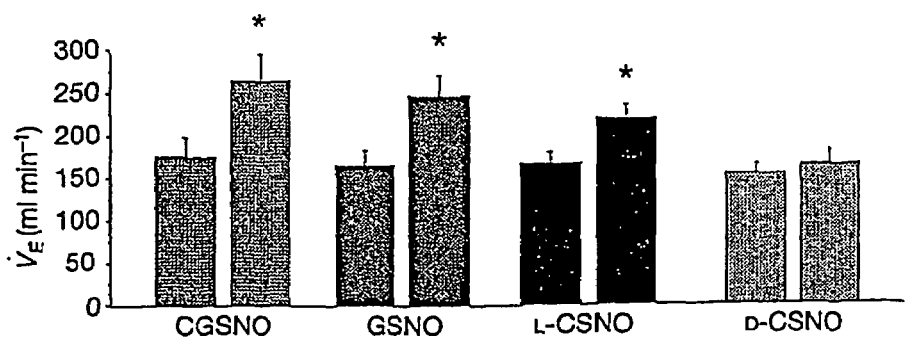

Applicants have discovered that S-nitrosothiols, including S-nitrosoglutathione (GSNO) dramatically increase minute ventilation ($V_E$) at the level of the brainstem respiratory control centers in the nucleus tractus solitarius (nTS), see FIG. 1. Furthermore, GSNO may be formed during blood deoxygenation and is present in µM concentrations in the mammalian brain stem. Applicants have also shown (see FIG. 2) that the GSNO-induced increase in $V_E$ is dependent on the presence and activity of an enzyme, γ-glutamyl transpeptidase (GGT). GGT breaks down GSNO to S-nitrosocysteinyl glycine (CGSNO). When GGT is inhibited, CGSNO, but not GSNO, increases minute ventilation. Importantly, GSNO has no effects on blood pressure or heart rate ("hemodynamic effects") in the same species. Therefore, GGT-dependent GSNO effects 1) stimulate increased ventilation; 2) translate the effect of hypoxia to signal a respiratory effect at the level of the brain stem; 3) separates respiratory from hemodynamic responses at the level of the nTS; and 4) are regulated by GGT.

This pathway can be exploited through the use of modifiers of S-nitrosoglutathione metabolism to treat disorders of the control of breathing. For example, such disorders can be treated by the administration of GSH or GSH-mimetics, by administration of additional S-nitrosothiol precursors, or by stimulation of GGT. In accordance with one embodiment the method comprises the step of administering to a individual suffering from a breathing disorder a compound selected from the group consisting of ethyl nitrite, glutathione, S-nitrosoglutathione, S-nitrosocysteinyl glycine, S-nitrosocysteine, N-acetyl cysteine, S-nitroso-N-acetyl cysteine and nitric oxide. In one preferred embodiment the nitrosylating agent is selected from the group consisting of N-acetyl cysteine, S-nitroso-N-acetyl cysteine, ethyl nitrite, glutathione and S-nitrosoglutathione.

N-acetyl cysteine, ethyl nitrite, nitric oxide, N-acetyl cysteine and glutathione represent S-nitrosothiol precursors that can be modified in vivo to become agents capable of nitrosylating proteins. Compositions comprising nitrosylating agents or S-nitrosothiol precursor compounds can be further supplemented with agents that stimulate GGT activity. In one alternative embodiment the composition used for treating disordered control of breathing comprises a stimulant of γ-glutamyl transpeptidase activity as the active agent. Compounds that stimulate GGT activity include retinoic acid and other retinols and stimulants of retinoic acid receptors, follicle stimulating hormone, ethoxyquin and other stimulants of GGT promoter III or inhibitors of GGT gene negative regulatory sites, glycine-glycine in conjunction with glutathione, prostaglandin E2 with diethylnitrosamine, and stimulants of the antioxidant response element promoter. The disorders of control of breathing that can be treated in accordance with the present invention include central apnea, central hypoventilation, impaired control or peripheral respiratory drive, respiratory fatigue complicating obstructive lung disease, obstructive sleep apnea, and impending respiratory failure.

The S-nitrosylating agents of the present invention can be formulated with pharmaceutically acceptable carriers, diluents, and solubilizing agents for administration to a patient in need of such therapy. Such administration can be, for example, by injection (in a suitable carrier, e.g., sterile saline or water), inhalation, oral, transdermal, rectal, vaginal, or other common route of administration. The route of administration selected will vary based on the condition to be treated and the S-nitrosylating agent used to treat the individual. For example, N-acetyl cysteine, S-nitroso-N-acetyl cysteine and S-nitrosoglutathione are suitable for oral or inhalation administration. Whereas NO is only suitable for inhalation.

In one embodiment an S-nitrosylating agent, such as S-Nitrosoglutathione or other S-nitrosothiols, is administered intravenously at a dose ranging from about 0.1 mg/ml/kg to 20 mg/ml/kg or more preferably from about 1 mg/ml/kg to 10 mg/ml/kg. In another embodiment, the S-nitrosylating agent is ethyl nitrite that is administered by atomizer, diluted in ethanol at a concentration of about 1-100 part per trillion, or 10 mg delivered orally three times per day orally. In an alternative embodiment nitric oxide is administered (especially for newborns) continuously by inhalation in air/oxygen in doses of 100-500 parts per trillion, or qid doses of 10 ppm, to increase red blood cell SNO stores.

When administered orally, the compounds of the present invention can be administered as a liquid solution, powder, tablet, capsule or lozenge. The nitrosylating agents can be used in combination with one or more conventional pharmaceutical additives or excipients used in the preparation of tablets, capsules, lozenges and other orally administrable forms. When administered as an intravenous solution, the nitrosylating agents can be admixed with conventional IV solutions.

In accordance with one embodiment pharmacological agents are provided to treat apnea, hypoventilation, impending respiratory failure and hyperventilation. In particular, in one embodiment a composition comprising a low molecular weight reduced thiol is administered to an individual to treat a disorder of control of breathing. More particularly, the composition comprises a reduced glutathione, N-acetylcysteine, cysteinylglycine, and L-cysteine or other agents that function to increase delivery of S-nitrosothiols to neural respiratory control centers. The composition is formulated with pharmaceutically acceptable carriers, diluents and excipients for administration via an oral, parenteral or inhalation route. In accordance with one embodiment, compositions comprising a reduced thiol are used to treat central hypoventilation associated with sleep, whether congenital (as in congenital central hypoventilation syndrome) or acquired (such as is seen in sleep apnea syndromes, including obstructive sleep apnea). When N-acetylcysteine (generic) is selected as the S-nitrosylating agent the preferred route of administration is orally in doses of 10 mg three times per day by mouth (or in the range of 0.5-1.0 mg/kg qid) for apnea.

In another embodiment of the present invention a method is provided for treating impaired respiratory drive associated with emphysema, chronic bronchitis, cystic fibrosis, α-1 antitrypsin deficiency and other causes of chronic obstructive pulmonary disease. The method comprises the step of administering a reduced thiol composition of the present invention. Furthermore the compositions of the present invention can be used to permit oxygen therapy in these patients, whose disease is characterized by a blunted response to carbon dioxide and a dependence on hypoxic ventilatory drive (which is in turn is blunted with supplemental oxygen therapy). The nitrosylating agents of the present invention can overcome such a blunted respiratory drive by directly stimulating the neural respiratory control centers located in the brain stem and the carotid body.

In another embodiment the reduced thiol compositions of the present invention are used to stimulate respiration in severe, hypoxic respiratory distress associated with impending respiratory failure. The goal of this therapy is to allow an increase in minute ventilation both through improved S-nitrosothiol delivery to the brain stem, and improved oxygen delivery to the periphery (to obviate the need for mechanical respiratory support). In accordance with one embodiment a method of treating blunted respiratory drive comprises the step of administering, preferably by intravenous injection, a composition comprising a nitrosylating agent selected from the group consisting of ethyl nitrite, glutathione, S-nitrosoglutathione, S-nitroso-L-cysteinyl glycine, S-nitrosocysteine, N-acetyl cysteine, S-nitroso-N-acetyl cysteine and nitric oxide.

In another embodiment of the present invention a method is provided for treating central apnea caused by brain stem lesions (including tumors, radiation injury, trauma, chronic scarring, bleeding such as aneurysms or arterial venous malformation, tethering of the spinal cord from Arnold Chiari malformation and/or brain stem compression from hydrocephalous, neonatal anemia and brain stem immaturity associated with the newborn and/or premature newborn state). The method comprises the steps of administering to a patient in need thereof, a composition comprising an S-nitrosylating agent, including ethyl nitrite, S-nitrosoglutathione, S-nitrosocysteinyl glycine, S-nitrosocysteine, nitroglycerine, nitroprusside, nitric oxide, S-nitrosoanastylcysteine, S-nitrosohemoglobin and S-nitrosoalbumin. The composition can be administered orally, parenterally or by inhalation.

The mechanism by which these nitrosylating agents act is to increase the concentration of circulating S-nitrosothiols and/or the S-nitrosylation of endogenous thiol groups in erythrocytes to have a net affect of increasing S-nitrosylation of neural respiratory control targets. In one embodiment compositions comprising S-nitrosylating agents are used to treat central hypoventilation associated with sleep, whether congenital (as in congenital central hypoventilation syndrome) or acquired (such as is seen in sleep apnea syndromes, including obstructive sleep apnea). In another embodiment the compositions comprising S-nitrosylating agents are used to treat impaired respiratory drive associated with emphysema, chronic bronchitis, cystic fibrosis, a-1 antitrypsin deficiency and other causes of chronic obstructive pulmonary disease. Furthermore, such compositions can be used to permit oxygen therapy in these patients, whose disease is characterized by a blunted response to carbon dioxide and a dependence on hypoxic ventilatory drive (which is in turn blunted with supplemental oxygen therapy), and thus stimulate respiration in severe, hypoxic respiratory distress associated with impending respiratory failure. The goal of this therapy is to allow an increase in minute ventilation both through improved S-nitrosothiol delivery to the brain stem, and improved oxygen delivery to the periphery (to obviate the need for mechanical respiratory support).

The present invention is also directed to any composition that effects an increase in S-nitrosocysteinyl glycine levels in vivo either directly or indirectly. For example a therapeutic composition may include one or more agents that result in an increased cleavage of S-nitrosoglutathione to active S-nitrosocysteinyl glycine (see FIG. 2). Such agents include stimulants of γ-glutamyl transpeptidase expression and/or γ-glutamyl transpeptidase activity. For example such stimulants include retinoic acid and other retinols and stimulants of retinoic acid receptors, follicle stimulating hormone, ethoxyquin and other stimulants of GGT promoter III or inhibitions of GGT gene negative regulatory sites, glycine-glycine in conjunction with glutathione, prostaglandin E2 with diethylnitrosamine, and stimulants of the antioxidant response element promoter. Compositions comprising such stimulants of GGT activity can be used in a method of treating central apnea caused by brain stem lesions (including tumors, radiation injury, trauma, chronic scarring, bleeding such as aneurysms or arterial venous malformation, tethering of the spinal cord from Arnold Chiari malformation and/or brain stem compression from hydrocephalous, neonatal anemia and brain stem immaturity associated with the newborn and/or premature newborn state).

In another embodiment, a composition comprising a stimulant of GGT is used to treat central hypoventilation associated with sleep, whether congenital (as in congenital central hypoventilation syndrome) or acquired (such as is seen in sleep apnea syndromes, including obstructive sleep apnea). Such a composition can also be used to treat impaired respiratory drive associated with emphysema, chronic bronchitis, cystic fibrosis, a-1 antitrypsin deficiency and other causes of chronic obstructive pulmonary disease. Further, these agents can be used to permit oxygen therapy in these patients, whose disease is characterized by a blunted response to carbon dioxide and a dependence on hypoxic ventilatory drive (which is in turn blunted with supplemental oxygen therapy) and stimulate respiration in severe, hypoxic respiratory distress associated with impending respiratory failure. The goal of this therapy would be to allow an increase in minute ventilation both through improved S-nitrosothiol delivery to the brain stem, and improved oxygen delivery to the periphery (to obviate the need for mechanical respiratory support).

Alternatively, the systemic use of an inhibitor of GGT such as acivicin can be used to treat respiratory alkalosis associated with psychiatric hyperventilation or salicylate toxicity. The method comprises administering a composition comprising an inhibitor of GGT to a patient suffering from psychiatric hyperventilation or salicylate toxicity. In addition, inhibition of GGT can also be used acutely to treat hyperventilation associated with psychiatric disorders and the toxicity of certain medications such as aspirin. Preferred routes of administration include oral, parenteral or inhalation.

The present invention also encompasses a pack or kit comprising a a nitrosylating agent selected from the group consisting of ethyl nitrite, glutathione, S-nitrosoglutathione, S-nitroso-L-cysteinyl glycine, S-nitrosocysteine, N-acetyl cysteine, S-nitroso-N-acetyl cysteine and nitric oxide, for treating disordered control of breathing. The kits of the present invention may further comprise reagents for detecting and monitoring the in vivo concentration of S-nitrosothiols as well as syringes and other materials for administering the nitrosylating agents of the present invention. The nitrosylating agents of the kit can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

EXAMPLE 1

SNOs stimulate respiratory centers of the NTS to increase $V_E$.

To test the hypothesis that SNOs stimulate respiratory centers of the NTS to increase $V_E$, the ability of endogenous SNOs to increase $V_E$ in freely behaving, conscious rats using whole-body plethysmography was examined. CSNO, GSNO and CGSNO (1 nmol each) caused equivalent increases in $V_E$, whereas D-CSNO had no effect (see FIG. 1; dose threshold for L-SNOs is 0.1 pmol). The exogenous NO donor, S-nitroso-N-acetyl-L-penicillamine, had similar but reduced effects (not shown). The L- and D-isomers of CSNO decayed at identical rates in rat brainstem homogenates (26% min-1 mg -1 protein each; P=not significant (NS)). Furthermore, neither excess 8-bromocyclic GMP nor glutathione had any effect on $V_E$ (n=3;P=NS).

Next, a low-mass fraction (less than a relative molecular mass of 10,000 (Mr 10K)) derived from deoxygenated blood was studied to determine whether the fraction would similarly increase $V_E$. This fraction reproduced precisely the effect of GSNO, L-CSNO and CGSNO, whereas the fraction from oxygenated blood was without effect. As expected, ultraviolet photolysis of the deoxygenated, blood-derived fraction (which causes homolytic cleavage of the SNO bond and liberation of free NO) completely eliminated its effect on $V_E$ (n=3). These observations suggest that SNOs arising during blood deoxygenation can signal an increase in $V_E$.

The normal physiological response to hypoxia was then studied in relation to the SNO effect on $V_E$. Exposure to a 10% oxygen environment resulted in an increase in $V_E$ identical to that produced by L-isomers of SNOs administered to the NTS (FIG. 1A). The decay characteristics for the recovery of $V_E$ after injection of GSNO were identical to those for recovery from hypoxia (FIGS. 1A & 1B). This recovery is characterized by a return of $V_E$ to baseline over approximately 3 min after return to normoxia. Taken together, these observations demonstrate that SNOs duplicate the physiological response of exposure to, and recovery from, hypoxia.

Figure 2A:
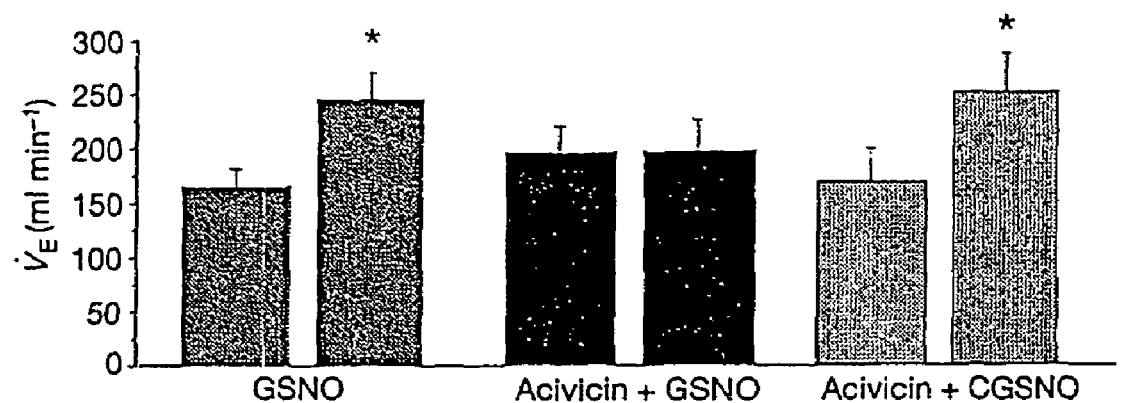
FIGS. 2A & 2B are bar graphs demonstrating the effect of γ-glutamyl transpeptidase (GGT) inhibition or deficiency on the ventilatory effects of SNOs.
Figure 2B:
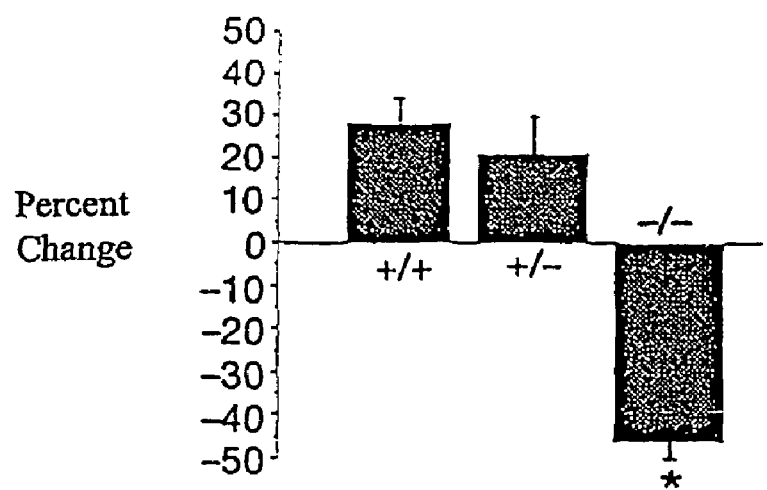

Endothelial transport and targeted neuronal biological activity of GSNO may depend, under certain circumstances, on biochemical modifications such as cleavage by GGT to form CGSNO. More particularly, NTS pre-treatment with the GGT inhibitor, acivicin, was found to attenuated GSNO-mediated increases in $V_E$, and that CGSNO overcame this inhibition (FIG. 2). Moreover, normal ventilatory offset (that is, the gradual return to baseline of $V_E$ after recovery from hypoxia that prevents apnea) was inhibited by acivicin. This suggests that GSNO is a critical precursor of CGSNO (and perhaps dipeptidase derived L-CSNO) in determining hypoxic ventilatory responses in vivo (FIG. 2). As expected, deoxygenated blood-derived CGSNO was found to be less stable than GSNO, consistent with a pathway by which GSNO is activated locally by GGT in neuronal tissue. Of note, this effect of GGT may distinguish respiratory stimuli to the NTS (which are reproduced by GSNO and are GGT dependent) from haemodynamic effects of SNOs, which although stereoselective are not reproduced by GSNO. This distinction may have pharmacological implications.

Finally, GGT was demonstrated to be required for the normal ventilatory response to hypoxia using a mouse deficient in GGT. Homozygous deficient mice had profound attenuation of hypoxic ventilatory recovery (FIG. 2C). These results show that endogenous SNOs act stereoselectively at the level of the NTS to produce the normal ventilatory response seen during hypoxia. This fits well with the proposal that SNOs may serve as signaling molecules between endothelial cells and central and peripheral neurons, as well as recent observations that (1) hemoglobin deoxygenation is associated with an increase in SNO formation and biological activity; and (2) neuronal tissues contain high levels of SNOs afferents from peripheral respiratory chemoreceptors project to areas of the NTS rich in NOS, which may produce SNOs; NOS expression by NTS is increased after chronic hypoxia; and hypoxic ventilatory responses are attenuated both by NOS inhibition and in endothelial NOS knockout mice.

In addition, a compound derived from deoxygenated, but not oxygenated, blood reproduces the ventilatory effect of hypoxia. This biological activity is physiologically identical to both exogenous SNOs and hypoxia itself, and was identified as GSNO by mass spectrometry. Both this SNO activity and hypoxia require GGT for normal signaling. Additional responses to hypoxia attributed to the transfer of nitrogen oxides from deoxygenated blood include vasodilation to maintain oxygen delivery and increases in endothelial gene expression mediated by hypoxia-inducible factor-1. S-nitrosothiol signaling is believed to be of central importance in the normal response to hypoxia, and it is anticipated that this pathway will provide targets for the development of new treatments for apnea Methods Measurement of $V_E$ A dual cannula (22G; Plastics One) was implanted close to the nucleus of the solitary tract according to standard stereotaxic coordinates (−14.0 mm bregma, 0.5 mm off midline, 7.0 mm depth; see Paxinos, G. & Watson, C. The Rat Brain in Stereotaxic Coordinates (Academic, New York, 1986), figure 74) through a hole drilled into the occipital skull of male Sprague-Dawley rats (approximately 250 g; pentobarbital anaesthesia). Placement was confirmed histologically after protocol completion. After recovery for 48 h (return to normal feeding and sleep/waking patterns), breath-by-breath ventilation was measured using the barometric method previously described (Gozal et al., J. Appl. Physiol. 81, 2068-2077 (1996)) after simultaneous, bilateral 0.1-ul injections in the freely behaving animal.

Plasma Preparation

Oxygenated blood drawn in an airtight syringe with GSH and EDTA (final concentrations 400 μM) by left ventricular puncture (rat) or peripherally (human) was maintained in 21% oxygen. Venous blood was reacted identically and was transferred to a hypoxia chamber under argon. Oxygen tension was measured electrochemically (Chirion). Samples underwent centrifugation (3,000 g for 5 min) followed by ultrafiltration (10K; Millipore), separation and selective ultraviolet photolysis (Jelight PS-3000-30; Laguna-Hills).

Preparation of and Assay for S-nitrosothiols

SNOs were prepared by acid nitrosation, titrated to pH 7.4 and maintained in EDTA in the dark at −80° C. until use to prevent decomposition. SNOs were detected by reduction/chemiluminescence as previously described (Fang et al., Biochem. Biophys. Res. Commun. 252, 535-540 (1998)). Briefly, samples were injected into 100 μM CuCl, 1 mM cysteine (pH 6; 50 8C) and purged with helium (grade 5; BOC Gases). Evolved NO was measured by chemiluminescence.

Mass Spectrometry

Samples eluted isocratically (90% of 0.1% formic acid, 10% methanol, 1.5 ml min$^{-1}$) over a Waters Symmetry C18 column (7.8×150 mm) were collected, lyophilized and reconstituted. Purified samples were injected onto a Waters C18 microbore column (1.0×150 mm) and analyzed by electrospray ionization mass spectrometry using a Finnigan LCQ Duo system. GSNO cations were monitored by selective ion monitoring at a mass to charge ratio (m/z) of 336.9. For mass spectrometry and mass spectrometry fragmentation experiments, GSNO cations were dissociated in the ion trap, and the fragments were monitored within a m/z range of 90±350.

The invention claimed is:

1. A method of increasing minute ventilation ($V_E$) at the level of the brainstem respiratory control centers in the nucleus tractus solitarius of an individual, said method comprising the step of administering to said individual a composition comprising an S-nitrosylating agent, wherein the S-nitrosylating agent is selected from the group consisting of ethyl nitrite, glutathione, S-nitroso-L-cysteinyl glycine, N-acetyl cysteine, and S-nitroso-N-acetyl cysteine.

2. The method of claim 1 wherein the S-nitrosylating agent is N-acetyl cysteine, and the composition is administered by inhalation.

3. The method of claim 1 wherein the S-nitrosylating agent is N-acetyl cysteine and the composition is administered orally.

4. The method of claim 1 wherein the S-nitrosylating agent is S-nitroso-N-acetyl cysteine, and the composition is administered by inhalation.

5. The method of claim 1 wherein the S-nitrosylating agent is S-nitroso-N-acetyl cysteine, and the composition is administered orally.

* * * * *